United States Patent [19]
Wright et al.

[11] Patent Number: 5,795,876
[45] Date of Patent: Aug. 18, 1998

[54] METHOD OF INHIBITING VASCULAR CELL ADHESION MOLECULE-1 AND TREATING CHRONIC INFLAMMATORY DISEASES WITH 2, 6-DI-ALKYL-4-SILYL-PHENOLS

[75] Inventors: Paul S. Wright, Cincinnati; Steven J. Busch, West Chester, both of Ohio

[73] Assignee: Hoechst Marion Rousssel, Inc., Cincinnati, Ohio

[21] Appl. No.: 824,221

[22] Filed: Mar. 25, 1997

Related U.S. Application Data

[60] Provisional application No. 60/070,902 Apr. 30, 1996.

[51] Int. Cl.$^6$ ............................................. A61K 31/695
[52] U.S. Cl. .................................................... 514/63
[58] Field of Search ............................................. 514/63

[56] References Cited

U.S. PATENT DOCUMENTS

| | | | |
|---|---|---|---|
| 3,129,262 | 4/1964 | Laufer | 260/578 |
| 3,576,883 | 4/1971 | Neuworth | 260/609 |
| 3,786,100 | 1/1974 | Neuworth | 260/590 |
| 3,862,332 | 1/1975 | Barnhart et al. | 424/337 |
| 3,897,500 | 7/1975 | Neuworth | 260/609 F |
| 4,663,314 | 5/1987 | Hayase et al. | 514/63 |
| 4,719,237 | 1/1988 | McCaughan | 514/712 |
| 4,734,527 | 3/1988 | Krauss | 568/47 |
| 4,772,363 | 9/1988 | Van Effen | 204/72 |
| 4,861,443 | 8/1989 | Van Effen | 204/72 |
| 4,870,101 | 9/1989 | Ku et al. | 514/476 |
| 4,900,757 | 2/1990 | Mao et al. | 514/712 |
| 4,975,467 | 12/1990 | Ku et al. | 514/712 |
| 5,008,421 | 4/1991 | Brownell et al. | 556/406 |
| 5,061,734 | 10/1991 | Mao et al. | 514/712 |
| 5,112,870 | 5/1992 | Mao et al. | 514/712 |
| 5,155,250 | 10/1992 | Parker et al. | 556/427 |
| 5,217,870 | 6/1993 | Hession et al. | 435/7.24 |
| 5,272,263 | 12/1993 | Hession et al. | 536/23.5 |
| 5,281,738 | 1/1994 | Parker et al. | 556/427 |
| 5,304,668 | 4/1994 | Parker et al. | 556/449 |
| 5,356,917 | 10/1994 | Panetta | 514/369 |
| 5,367,056 | 11/1994 | Hession et al. | 530/380 |
| 5,380,747 | 1/1995 | Medford et al. | 514/423 |
| 5,401,883 | 3/1995 | Laskovics et al. | 568/47 |
| 5,608,095 | 3/1997 | Parker et al. | 556/413 |

FOREIGN PATENT DOCUMENTS

| | | |
|---|---|---|
| 9460533 | 4/1993 | Australia . |
| 0374048 | 12/1989 | European Pat. Off. . |
| 7330595 | 12/1995 | Japan . |
| 1199871 | 5/1968 | United Kingdom . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9414786 | 7/1994 | WIPO . |
| 9416094 | 7/1994 | WIPO . |
| 9417828 | 8/1994 | WIPO . |
| 9504749 | 2/1995 | WIPO . |

OTHER PUBLICATIONS

Miller, "High Density Lipoproteins and Atherosclerosis", Ann. Rev. Med. 1980 31:97–108.

Brown et al, "Lipoprotein Metabolism in the Macrophage: Implications for Cholestrol Deposition in Atherosclerosis", Ann. Review Biochem., 1983, 52:223–61.

Maciejko et al, "Apolipoprotein A–1 as a marker of angiographically assessed coronary–artery disease", The New England Journal of Medicine, 309:385–389 (Aug. 18, 1983).

Mao et al, "Immunochemistry of human plasma high density lipoproteins . . . " Biochemistry, 1975, 14, pp. 4127.

Badimon et al, "Quantification and immunolocalization of apolipoprotein E . . . ", Atherosclerosis, 61 (1986) 57–66.

Mao et al, "Immunochemistry of human plasma high density lipoproteins . . . ", Biochemistry, vol. 14, No. 18, 1975, pp. 4127–4131.

Kita et al, "Probucol prevents the priogression of atherosclersis in Watanabe heritable . . . " Medical Sciences, vol. 84, pp. 5928–5931, Aug. 1987.

Carew et al, "Antiatherogenic effect of probucol unrelated to its hypocholesterolemic effect: . . . " Medical Sciences, vol. 84, pp 7725–7729, Nov. 1987.

Parthasarathy, et al, "Probucol inhibits oxidative modification of low density lipoprotein", J. Cin. Invest., vol. 77, Feb. 1986, pp. 641–644.

Product Labeling for Lorelco, Physician's Desk Reference, 42nd edition, (1988), Medical Economics Co., Inc., Oradell, N.J.

(List continued on next page.)

*Primary Examiner*—Phyllis G. Spivack
*Attorney, Agent, or Firm*—William R. Boudreaux; David M. Stemerick

[57] ABSTRACT

Methods useful for inhibiting VCAM-1 and for treating chronic inflammatory conditions in a patient in need thereof are disclosed comprising administering to the patient effective amounts of a compound of the formula

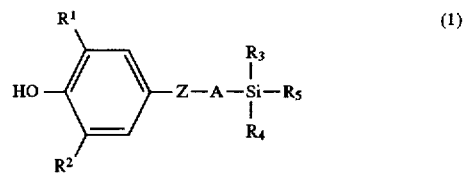

(1)

wherein
$R_1$, $R_2$, $R_3$ and $R_4$ are each independently a $C_1$–$C_6$ alkyl group;
Z is a thio, oxy or methylene group;
A is a $C_1$–$C_4$ alkylene group;
$R_5$ is a $C_1$–$C_6$ alkyl or —$(CH_2)_n$—(Ar)
wherein n is an integer 0, 1, 2 or 3; and Ar is phenyl or naphthyl unsubstituted or substituted with one to three substituents selected from the group consisting of hydroxy, methoxy, ethoxy, chloro, fluoro or $C_1$–$C_6$ alkyl; are disclosed.

46 Claims, 1 Drawing Sheet

OTHER PUBLICATIONS

Steinberg, "Studies on the Mechanism of Action of Probucol", The American Journal of Cardiology, /vol. 57, pp. 16H–21H.

Satonin et al, "Comparison of gas chromatography and high-performance liquid chromatography for the analysis of probucol in plasma" Journal of Chromatography, 380 (1986) pp. 401–406.

Mao et al, "Monoclonal Antibodies to human . . . I", Clinical Chemistry, vol. 29, No. 11, 1983, pp. 1890–1897.

Patton et al, "Monoclonal Antibodies to human . . . II", Clinical Chemistry, vol. 29, No. 11, 1983 pp. 1898–1903.

Gotteland et al, J. Med. Chem., 1995, 38, pp. 3207–3216.

Pilewski et al, Am. J. Respir. Cell Mol. Biol. vol. 12, pp. 1–3, 1995.

Marui et al, American Society for Clinical Investigation, Inc. vol. 92, Oct., 1993, pp. 1866–1874, Vascular Cell Adhesion Molecule–1.

Boschelli et al, J. Med. Chem. 1995, 38, pp. 4597–4614, Inhibition of E–Selection–, ICAM–1–, and VCAM–1–.

Newman et al, FASEB Journal, Federation of American Societies for Experimental Biology, Mar. 10, 1995, vol. 9, No. 4 (Abstract).

Derwent Abstract, 94–322148/40 (1994).

Derwent Abstract, 94–322152/40 (1994).

Abstract 009, Pres. made at 211th ACS National Meeting, Mar. 24–28, 1996, Medicinal Chemical Division. Ref. Bioorganic & Medicinal Chemistry Letter, vol. 6, pp. 533–538, 1996.

Derwent Abstract, 94–325887/41 (1994).

Alerting Bulletin 92–324750/49 Abbreviated Abstract for JP06505732–W (1992).

Alerting Bulletin 92–332847/41 Abbreviated Abstract for JP06505735–W (1992).

METHOD OF INHIBITING VASCULAR CELL ADHESION MOLECULE-1 AND TREATING CHRONIC INFLAMMATORY DISEASES WITH 2, 6-DI-ALKYL-4-SILYL-PHENOLS

This application claims the benefit of U.S. Provisional application Ser. No. 60/070,902, filed Apr. 30, 1996.

BACKGROUND OF THE INVENTION

Vasular cell adhesion molecule-1 (VCAM-1) and intercellular adhesion molecule-1 (ICAM-1) are adhesion molecules in the immunoglobulin superfamily that are upregulated in vascular endothelial and smooth muscle cells by cytokines, such as, for example, interleukin-1 (IL-1), interleukin-4 (IL-4) and tumor necrosis factor-α (TNF-α). Through interaction with the appropriate integrin counter receptor, VCAM-1 and ICAM-1 mediate adhesion and transendothelial migration of leukocytes in inflammatory responses. Inhibitors of VCAM-1 and/or ICAM-1 have therapeutic applications for many types of chronic inflammatory disorders including asthma, rheumatoid arthritis, and autoimmune diabetes. For example, it is known that the expression of VCAM-1 and ICAM-1 are increased in asthmatics. Pilewski, J. M. et al., Am. J. Respir. Cell Mol. Biol. 12, 1–3 (1995); Ohkawara, Y. et al., Am. J. Respir. Cell Mol. Biol. 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, H. A. et al., Am. J. Respir. Care Med. 149, 1186–1191 (1994).

Furthermore, VCAM-1 is also involved as a mediator in other chronic inflammatory disorders such as rheumatoid arthritis and autoimmune diabetes. For example, there is increased expression of endothelial adhesion molecules, including VCAM-1, in the microvasculature of rheumatoid synovium. Koch, A. E. et al, Lab. Invest. 64, 313–322 (1991); Morales-Ducret, J. et al., Immunol. 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., Proc. Natl. Acad. Sci. USA 90, 10494–10498 (1993); Burkly, L. C. et al., Diabetes 43, 523–534 (1994); Baron, J. L. et al., J. Clin. Invest. 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Orocz, C. G. et al., Immunol. Lett. 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. E. et al., Nature 376, 517–519 (1995). Inhibitors of the expression of soluble VCAM-1 have potential therapeutic value in treating diseases with a strong angiogenic component, including tumor growth and metastasis. Folkman, J., and Shing, Y., J. Biol. Chem. 10931–10934 (1992).

The promoters for both VCAM-1 and ICAM-1 have been cloned and characterized. For example, both promoters contain multiple DNA sequence elements which can bind the transcription factor, NF-kB. Iademarco, M. F. et al., J. Biol. Chem. 267, 16323–16329 (1992); Voraberger, G. et al., J. Immunol. 147, 2777–2786 (1991). The NF-kB family of transcription factors is central in the regulation of several genes upregulated within sites of inflammation. The activation of NF-kB as a transcription factor involves dissociation from an inhibitory subunit, IkB, in the cytoplasm. NF-kB subunits translocate to the nucleus, bind to specific DNA sequence elements, and activate transcription of several genes, including VCAM-1 and ICAM-1. Collins T. et al., Lab. Invest. 68, 499–508 (1993).

It has been postulated that regulation of VCAM-1 gene expression may be coupled to oxidative stress through specific reduction-oxidation (redox) sensitive transcriptional or posttranscriptional regulatory factors. The antioxidants pyrollidine dithiocarbamate and N-acetylcysteine inhibit cytokine-induced expression of VCAM-1, but not ICAM-1 in vascular endothelial cells. Mauri, N. et al., J. Clin. Invest. 92, 1866–1874 (1993). This would indicate that the inhibition of VCAM-1 expression by antioxidants involves some additional factors not involved in the regulation of ICAM-1 expression.

2,6-Di-alkyl-4-silyl-phenols are disclosed as antiatherosclerotic agents by Parker et al. in U.S. Pat. No. 5,155,250, issued Oct. 13, 1992. Furthermore, 2,6-Di-alkyl-4-silyl-phenols are disclosed as serum cholestrol lowering agents in PCT International Publ. No. WO 95/15760, published Jun. 15, 1995.

It would be advantageous to control the release of VCAM-1, and to treat VCAM-1 mediated effects. It would also be advantageous to control or treat VCAM-1 inflammation, without production of concomitant side effects known to accompany the use of antiinflammatory steroids and non-steroidal antiinflammatory agents.

SUMMARY OF THE INVENTION

It has now been found that compounds corresponding to the formula

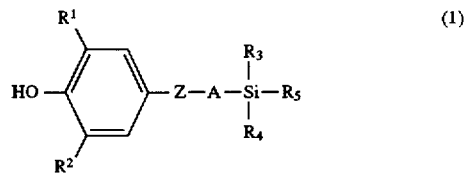

wherein $R_1$, $R_2$, $R_3$ and $R_4$ are each independently a $C_1$–$C_6$ alkyl group;

Z is a thio, oxy or methylene group;

A is a $C_1$–$C_4$ alkylene group;

$R_5$ is a $C_1$–$C_6$ alkyl or —$(CH_2)_n$—(Ar)

wherein n is an integer 0, 1, 2 or 3; and Ar is phenyl or naphthyl unsubstituted or substituted with one to three substituents selected from the group consisting of hydroxy, methoxy, ethoxy, chloro, fluoro or $C_1$–$C_6$ alkyl can be used to inhibit the cytokine-induced expression of VCAM-1. Such compounds can be administered to patients to inhibit VCAM-1; to inhibit or treat VCAM-1 mediated effects; and to inhibit or treat VCAM-1 mediated inflammation. The compounds can be administered to inhibit or treat VCAM-1 mediated effects in conditions such as chronic inflammation, asthma, rheumatoid arthritis and autoimmune diabetes.

DETAILED DESCRIPTION OF THE INVENTION

Figure 1:
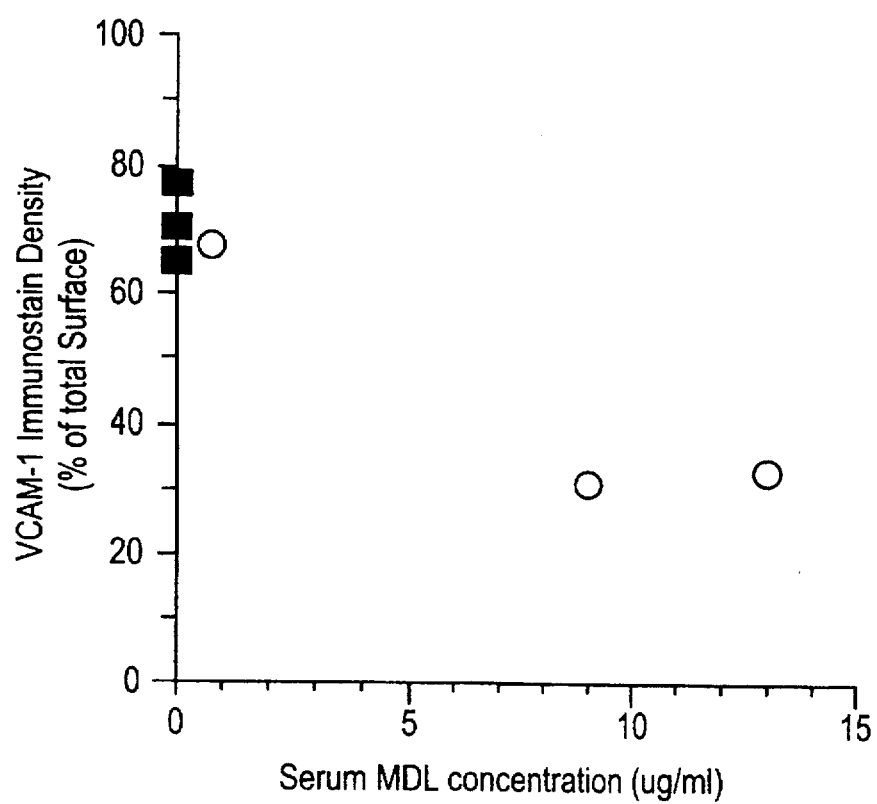
FIG. 1 illustrates the effect of 2,6-di-t-butyl-4-[(dimethylphenylsilyl)methylthio]phenol (MDL 29,353) on LPS induced VCAM-1 expression in rabbit aorta in vivo. Data are expressed as the percent of the aortic surface endothelium expressing VCAM-1 as measured by immunostaining with an anti-rabbit VCAM-1 antibody.

As used herein, the term "$C_1$–$C_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

Likewise, the term "$C_1$–$C_4$ alkylene" refers to a saturated hydrocarbyldiyl radical of straight or branched configuration made up of from one to four carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like.

In those instances wherein $R_5$ is a —$(CH_2)_n$—(Ar) radical, the "—$(CH_2)_n$—" moiety represents a saturated hydrocarbyldiyl radical of straight chain configuration. The term "n" is defined as an integer 0, 1, 2 or 3. The moiety "—$(CH_2)_n$—" thus represents a bond, methylene, 1,2-ethanediyl or 1,3-propanediyl. The "—(Ar)" moiety represents an aryl radical defined as a substituted or unsubstituted phenyl or napthyl group. In those instances wherein the —(Ar) moiety is a substituted aryl, the phenyl or napthyl can bear from 1 to 3 substituents in any position otherwise occupied by a hydrogen atom. Substituents are selected from the group consisting of hydroxy, methoxy, ethoxy, chloro, fluoro and $C_1$–$C_6$ alkyl group. Specifically included within the scope of the term "—$(CH_2)_n$—(Ar)" are phenyl; napthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The compounds of formula (1) can be prepared by utilizing procedures and techniques well known and appreciated by one of ordinary skill in the art. A general synthetic scheme for preparing compounds of formula (1) wherein Z is sulfur or oxygen is set forth in Scheme A, wherein all substituents, unless otherwise indicated, are previously defined.

SCHEME A

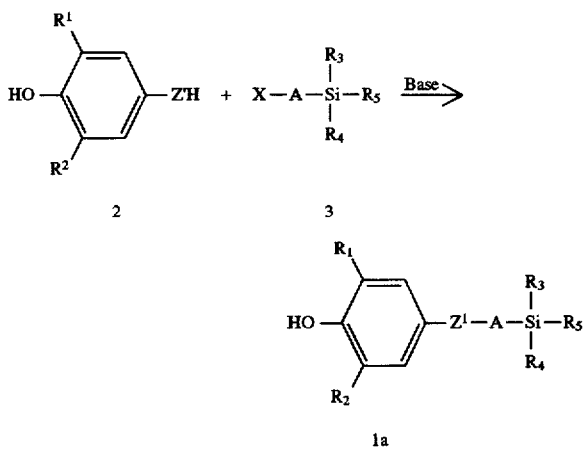

Z = S or O
X = chlorine, bromine, or iodine

In general, a phenol of structure 1a can be prepared by reacting the appropriate 2,6-dialkyl-4-mercaptophenol or 2,6-dialkylhydroquinone of structure 2 (or suitably protected derivatives) with a non-nucleophilic base, such as sodium hydride, potassium carbonate or cesium carbonate, and the appropriate haloalkylenesilane of structure 3, such as the appropriate chloroalkylenesilane, in a suitable aprotic solvent, such as acetonitrile, dimethylformamide or dimethylacetamide, or in an aqueous solvent, such as water/2-butanone.

Starting materials for use in the general synthetic procedure outlined in Scheme A are readily available to one of ordinary skill in the art. For example, certain phenol starting materials for various compounds of formula (1) wherein Z is sulfur, such as 2,6-di-tertiarybutyl-4-mercaptophenol, are described in U.S. Pat. No. 3,576,883, U.S. Pat. No. 3,952,064, U.S. Pat. No. 3,479,407 and in Japanese Patent Application 73-28425. Also, silyl starting materials for various compounds of formula (1), such as (trimethylsilyl)-methyl iodide, (trimethylsilyl)methyl bromide, (trimethyl-silyl) methyl chloride, (1-chloropropyl)trimethylsilane, are described in *Synthesis* 4, 318–19 (1988) and *J. Am. Chem. Soc.* 105, 5665–75 (1983). Additional methods for preparing suitable silanes include a Grignard reaction e.g. 4-Bromoanisole is reacted with magnesium metal to form the Grignard reagent and the reagent is reacted with chlorodimethyl chloromethyl silane to give chloromethyldimethyl-4-methoxy phenyl silane.

Grignard reagent

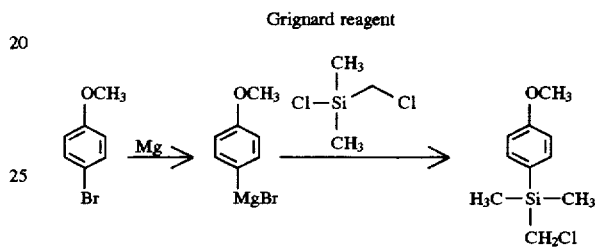

Alternatively, anisole may be lithiated by reacton with Δ-Butylithium and the lithio compound formed is reacted with chlorodimethyl chloromethyl silane to give chloromethyl dimethyl-2-methoxyphenyl silane.

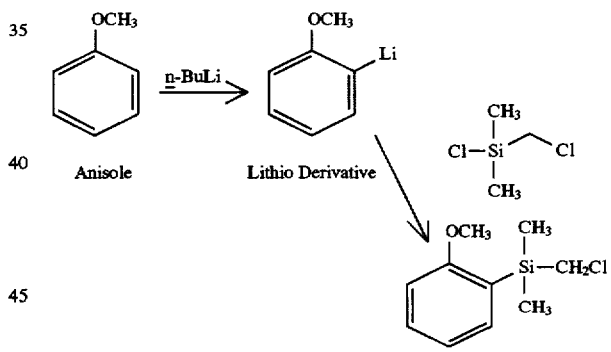

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

In those instances where $R_1$ and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "mp" refers to melting point; "mg" refers to milligrams; "µM" refers to micromolar; "µg" refers to micrograms.

EXAMPLE 1

2,6-Di-t-butyl-4-[(dimethylphenylsilyl)methylthio]phenol (MDL 29,353)

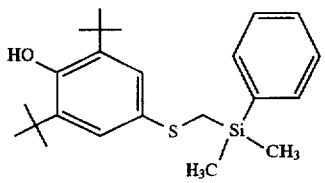

Mix 2,6-di-t-butyl-4-mercaptophenol (2.4 g, 10 mmol), potassium carbonate (1.4 g, 10 mmol), chloromethyldimethylphenylsilane (1.9 g, 10 mmol) and dimethylformamide (50 mL) and stir overnight at room temperature under argon atmosphere. Dilute the mixture with ice-water and extract with ethyl ether. Wash the ethereal layer with water, then brine, filter through flourosil-$Na_2SO_4$, and evaporate to an orange oil (3.5 g). Purify the product by first distilling (bp 160°–170° C. @0.1 mm Hg), then subjecting to silica gel chromatography ($CCl_4$:$CHCl_3$/1:1) to obtain the title compound as a light yellow oil which slowly crystallizes to a white waxy solid (2.3 g, 59%).

Anal. Calcd for $C_{23}H_{34}OSSi$: C, 71.44; H, 8.86; S, 8.29; Found: C, 71.14; H, 8.86; S, 7.98.

EXAMPLE 2

2,6-Di-t-butyl-4-[(trimethylsilyl)methylthio]phenol (MDL 28,235)

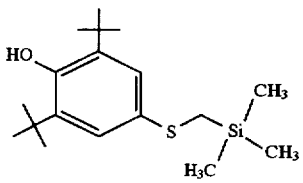

Mix 2,6-di-t-butyl-4-mercaptophenol (2.4 g, 10 mmol), potassium carbonate (1.4 g, 10 mmol), and dimethylacetamide (50 mL) and stir at room temperature under argon atmosphere. Add chloromethyltrimethylsilane (1.3 g, 10 mmol) and stir overnight. Warm on a steam bath for 2 hours, cool, and dilute with water. Extract with ethyl ether, dry, evaporate to a light yellow solid (2.8 g) and recrystallize ($CH_3CN$) to give 1.1 g (34%) of the title compound; mp 100°–101° C.

Anal. Calcd for $C_{18}H_{32}OSSi$: C, 66.60; H, 9.88; S, 9.88; Found: C, 66.83; H, 10.05; S, 9.91.

EXAMPLE 3

2,6-Dimethyl-4-[(trimethylsilyl)methyloxy]phenol

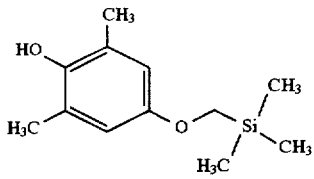

Mix 2,6-dimethylhydroquinone (1.4 g, 10 mmol), potassium carbonate (1.4 g, 10 mmol), chloromethyltrimethylsilane (1.9 g, 10 mmol) and dimethylformamide (50 mL). Stir at room temperature under inert atmosphere until the reaction is complete. Dilute the mixture with ice-water and extract with ethyl ether. Wash the ethereal layer with water, then brine and filter through fluorosil-$Na_2SO_4$. Evaporate to give the title compound and purify by silica gel chromatography.

EXAMPLE 4

2,6-Di-t-butyl-4-[(4-chlorophenyldimethylsilyl)methyloxy] phenol (MDL 104,280)

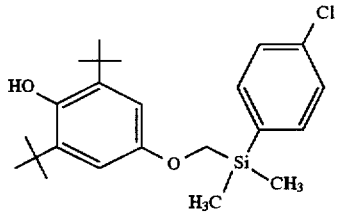

Reflux 2,6-di-t-butylbenzhydroquinone (13.7 g, 61.6 mM), potassium carbonate (9.4 g, 68 mM), chloromethyl (4-chlorophenyl) dimethyl silane ( 14.9 g, 68 mM) and a catalytic amount of potassium iodide in acetonitrile (200 ml) for three days under $N_2$. Filter off solids and evaporate. Redissolve in ethyl acetate and wash with water, then brine, dry with anhydrous magnesium sulfate, filter and evaporate. The resulting orange oil can be purified by distilling to 135° C. @0.1 mm Hg to remove lower boiling impurities followed by distillation of product (bp °C. @0.1 mm Hg). The product which crystallizes on standing can be recrystallized from hexane to give fine white needles (7.4 g, 27% yield ) mp 102°–105° C.

Anal. Calcd. for $C_{23}H_{33}ClO_2Si$: C, 68.20; H, 8.21 Found: C, 68.39; H, 8.13 NMR ($CDCl_3$) : 7.53 (d, 2H, J 8.3), 7.34 (d, 2H, J 8.3) 6.79 (s, 2H), 4.73 (s, 1H), 3.71 (s, 2H), 1.42 (s, 18H), 0.41 (s, 6H).

EXAMPLE 5

2,6-Di-t-butyl-4-[(dimethyl-4-fluorophenylsilyl)methyloxy]phenol (MDL 104,389)

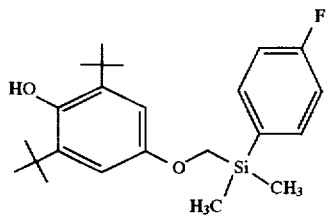

Reflux 2,6-di-t-butylbenzhydroquinone (10.0 g, 45 mM), potassium carbonate (6.2 g, 45 mM) and dimethyl (4-flurophenyl) iodomethylsilane (13.2 g, 45 mM) in acetonitrile (150 ml) for three days under nitrogen. Filter off solids and evaporate. Redissolve in ethyl acetate and wash with water, then brine, dry with anhydrous magnesium sulfate, filter and evaporate to a very pale yellow oil which crystallizes on standing. This material could be recrystallized from methanol to give a white crystalline solid (5.9 g, 34% yield) mp 90°–93° C.

Anal. calcd. for $C_{23}H_{33}FO_2Si$: C, 71.09; H, 8.86 Found: C, 70.96; H, 8.58 NMR (CDCl$_3$): 7.58 (dd, 2H, J 8.5, 6.2), 7.10–7.04 (m, 2H), 6.80 (s, 2H), 4.73 (s, 1H), 3.71 (si, 2H), 1.43 (s, 18H), 0.41 (s, 6H).

EXAMPLE 6

2,6-Di-t-butyl-4-[(dimethylphenylsilyl)methyloxy]phenol (MDL 103,902)

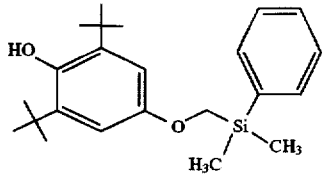

Reflux 2,6-di-t-butylbenzhydroquinone (5.43 g, 24.4 mM), potassium carbonate (3.7 g, 26.8 mM) and dimethyl (iodomethyl) phenylsilane (7.4 g, 26.8 mM) in acetonitrile (125 ml) overnight under N$_2$. Filter off solids and evaporate. Redissolve in ethyl acetate and wash with water, then brine, dry with anhydrous magnesium sulfate, filter and evaporate. The resulting orange oil can be purified by distilling to 135° C. @0.1 mm Hg. to remove lower boiling impurities followed by distillation of product (bp 155°–165° C. @0.1 mm Hg). The product which crystallizes on standing can be recrystallized from methanol to give a white solid (5.8 g, 64% yield) mp 82°–83° C. Anal. Calcd. for $C_{23}H_{34}O_2Si$: C, 74.54; H, 9.25 Found: C, 74.51; H, 9.28 NMR (CDCl$_3$): 7.64–7.58 (m, 2H), 7.42–7.32 (m, 2H), 6.80 (s, 2H), 4.72 (s, 1H), 3.73 (s, 2H), 1.42 (s, 18H), 0.42 (s, 6H).

EXAMPLE 7

2,6-Di-t-butyl-4-[(dimethyl-4-methoxyphenylsilyl) methyloxy]phenol (MDL 105,074)

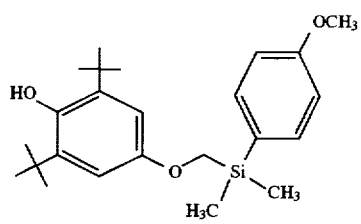

Reflux 2,6-di-t-butylbenzhydroquinone (13.7 g, 61.1 mM), potassium carbonate (9.4 g, 68 mM), chloromethyl (dimethyl)-4-methoxyphenylsilane (14.6 g, 68 mM) and a catalytic amount of potassium iodide in acetonitrile (200 ml) for three days under N$_2$. Filter off solids and evaporate. Redissolve in ethyl acetate and wash with water, then brine, dry with anhydrous magnesium sulfate, filter and evaporate. The resulting orange oil can be purified by distilling to 135° C. @0.1 mm Hg to remove lower boiling impurities followed by distillation of product (bp 155°–165° C. @0.1 mm Hg). The product which crystallizes on standing can be recrystallized from hexane to give a white solid (4.9 g, 19% yield) mp 122°–123° C.

Anal. Calcd. for $C_{24}H_{36}O_3Si$: C, 71.95; H, 9.06 Found: C, 71.80; H, 9.00 NMR (CDCl3): 7.53 (d, 2H, J 8.6), 6.93 (d, 2H, J8.6), 6.80 (s, 2H), 4.71 (s, 1H), 3.81 (s, 3H), 3.70 (s, 2H), 1.42 (s, 18H), 0.39 (s, 6H).

EXAMPLE 8

2,6-Dimethyl-4-[(dimethylphenylsilyl)methyloxy]phenol (MDL 103,719)

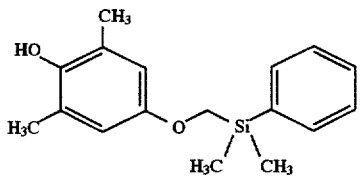

Reflux 2,6-dimethylhydroquinone (10.0 g, 72.4 mmol), potassium carbonate (10.0 g, 72.4 mmol), and dimethyl (chloromethyl)phenylsilane (13.4 g, 72.4 mmol in acetonitrile (150 ml) for 72 hours under argon. The mixture is allowed to cool and diluted with water and extracted into ether. The oil is distilled at 145° to 160° C. @0.1 mm Hg. to give 4.9 g. of a light yellow oil.

Anal. Calcd. for $C_{17}H_{22}O_2Si$: C, 71.28; H, 7.74 Found: C, 71.27; H, 7.74

EXAMPLE 9

2-t-butyl-6-methyl-4-[(dimethylphenylsilyl)methylthio] phenol (MDL 104,518)

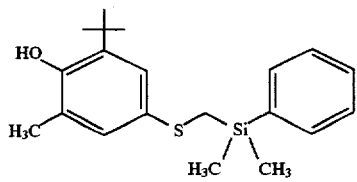

Reflux 2-t-butyl-6-methyl-4-mercaptophenol (11.8 g, 60.1 mmol), potassium bicarbonate (6.0 g, 11.8 mmol), and dimethyl(chloromethyl)phenylsilane (11.1 g 60.1 mmol) in isopropanol (150 ml) for 24 hours under argon. The mixture is allowed to cool and diluted with water and extracted into ether. The ether layer was evaporated to dryness to give 21.9 g of an oil. The oil is distilled at 145°–160° C. (0.1 mmHg) to give 5.5 g of a light yellow oil.

Anal. Calcd for $C_{20}H_{28}OSSi$: C, 69.71; H, 8.19 Found: C, 69.76, H, 8.20

EXAMPLE 10

2,6-Di-t-butyl-4-|(dimethyl-2-methoxyphenylsilyl) methyloxy|phenol (MDL 104,036)

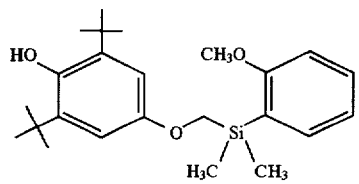

A mixture of chloromethyldimethyl (2-methoxy) phenylsilane (27.2 g, 0.127 mol), sodium iodide (19 g, 0.127 mol) and acetonitrile (350 mL) was heated at reflux for 28 h. The mixture was cooled to ambient temperature and 2,6-di-t-butyl-1,4-hydroquinone (31.5 g, 0.14 mol) and potassium carbonate (20.8 g, 0.15) mole were added. The mixture was refluxed under a nitrogen atmosphere for 7 days. The mixture was cooled, poured into water (400 mL) and ethyl acetate (400 mL) and the organic layer was separated. The organic layer was evaporated and the residue was chromatographed on silica gel (hexane/ethyl acetate 9/1). The chromatographed product was recrystallized (methanol) to give the product (15.6 g, 31%) as a white solid, mp 89°–90° C.

Anal. Calcd for $C_{24}H_{36}O_3Si$: C, 71.95; H, 9.06 Found: C, 71.84; H, 9.05.

EXAMPLE 11

2,6-Di-t-butyl-4-[(dimethyl-2,5-dimethoxyphenylsilyl) methyloxy]phenol (MDL 103,016)

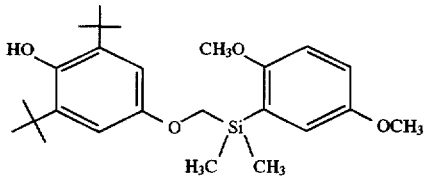

Preparation as for previous compound using chloromethyl dimethyl-2,5-dimethoxy-phenyl silane (14 g, 57 mmol) as the silane to give a white solid, mp 103°–04° C.

Anal. Calcd for $C_{25}H_{38}O_4Si$: C, 69.72; H, 8.89 Found: C, 69.71; H, 8.72.

EXAMPLE 12

2,6-Di-t-butyl-4-|(dimethyl-2,3-dimethoxyphenylsilyl) methyloxy|phenol (MDL 108,750)

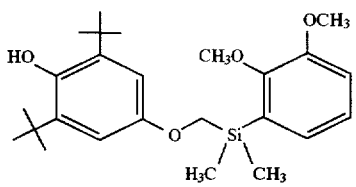

Preparation as above using chloromethyl (dimethyl)-2,3-dimethoxy phenyl silane (11.3 g, 46 mmol) as the silane to give a white solid, mp 94.5°–96° C.

Anal. Calcd for $C_{25}H_{38}O_4Si$: C, 69.72; H, 8.89 Found: C, 69.84; H, 8.91.

EXAMPLE 13

2,6-Di-t-butyl-4-|(dimethyl-4-t-butylphenylsilyl) methyloxy|phenol (MDL 106,630)

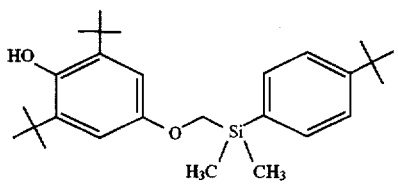

Preparation as above using 4-t-Butylphenyl chloromethyl dimethyl silane (6.2 g, 25.7 mmol) as the silane to give the product as a white solid, mp 114°–115° C.

Anal. Calcd for $C_{27}H_{42}O_2Si$: C, 76.00; H, 9.92 Found: C, 75.94; H, 10.13.

EXAMPLE 14

2,6-Di-t-butyl-4-|(benzyldimethylsilyl)methyloxy|phenol (MDL 107,411)

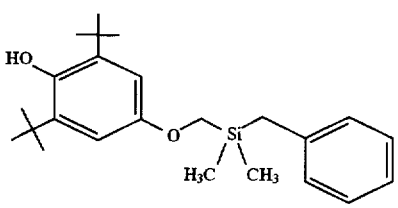

Preparation as above using benzyl chloromethyl dimethyl silane (7.13 g, 35.9 mmol) as the silane to give the product as a white solid, mp 76°–77° C.

Anal. Calcd for $C_{24}H_{36}O_2Si$: C, 74.95; H, 9.43 Found: C, 74.94; H, 9.36.

EXAMPLE 15

2.6-Di-t-butyl-4-|(dimethyl-p-methoxybenzylsilyl) methyloxy|phenol (MDL 108.816)

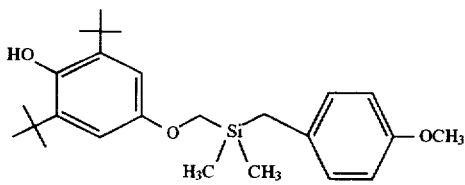

Step a: Preparation of dimethyl-p-methoxybenzylchloromethylsilane: Stir magnesium turnings (9.7 g, 0.4 g atom) with a Teflon® paddle overnight under nitrogen. Suspend this "activated" magnesium in dry THF (100 mL) and add a crystal of iodine. Add a solution of p-methoxybenzylbromide (80.8 g, 0.4 mol) in THF (400 mL) to this suspension at such a rate as to maintain a gentle reflux. Once the addition is complete, continue the stirring (~2 h) until nearly all of the magnesium is consumed. Add a solution of dimethylchloromethylchlorosilane (52.7 mL, 0.4 mol) in THF (200 mL) dropwise, and stir the mixture overnight at room temperature. Quench the reaction mixture with saturated aqueous ammonium chloride (500 mL) and stir at room temperature (~2 hrs.). Filter the precipitated magnesium salts and dilute with ether (300 mL). Separate the organic phase, wash with water (3×250 mL), saturated aqueous sodium chloride (3×250 mL), dry with anhydrous magnesium sulfate, filter and evaporate. Purify the resulting brown oil by distillation to provide the title compound. Yield 55%, bp 110°–115° C. at 5 mm Hg.

Anal Calcd for $C_{10}H_{15}ClOSi$: C, 55.93, H 7.15. Found: C, 55.40, H, 7.15.

Step b; Preparation of 2.6-Di-t-butyl-4-[(dimethyl-p-methoxybenzyl-silyl)methyloxy]phenol (MDL 108.816): Heat a mixture of dimethyl-p-methoxybenzyl-chloromethylsilane (28 g, 0.13 mol), sodium iodide (0.5 g, cat), 2,6-di-t-butybenzhydroquinone (23 g, 0.1 mol) and cesium carbonate (32 g, 0.1 mol) in acetonitrile (250 mL) at reflux for 6 days, cool and pour into a mixture of water/ethyl acetate (400 mL each). Isolate the organic layer, dry, evaporate and heat the residue on a Kugelrohr apparatus at 110° C. (0.1 mm) for 3 hours and at 140°–160° C. for another 2 hours. The residue is solidified on standing to give the product (20.9 g, 39%) as a waxy solid, mp 58°–60° C.

Anal. Calcd for $C_{25}H_{38}O_3Si$: C, 72.41, H, 8.87. Found: C, 70.29, H, 8.96.

The following compounds can be prepared by procedures analogous to those described above in Examples 1–14:
2,6-di-t-butyl-4-[(triethylsilyl)methylthio]phenol
2,6-di-t-butyl-4-[(diethylphenylsilyl)methylthio]phenol
2,6-di-t-butyl-4-[(tripropylsilyl)methylthio]phenol
2,6-di-t-butyl-4-[(dipropylphenylsilyl)methylthio]phenol
2,6-di-t-butyl-4-[(triisopropylsilyl)methylthio]phenol
2,6-di-t-butyl-4-[(diisopropylphenylsilyl)methylthio]phenol
2,6-di-t-butyl-4-[(tributylsilyl)methylthio]phenol
2,6-di-t-butyl-4-[(dibutylphenylsilyl)methylthio]phenol
2,6-di-t-butyl-4-[(triisobutylsilyl)methylthio]phenol
2,6-di-t-butyl-4-[(diisobutylphenylsilyl)methylthio]phenol
2,6-di-t-butyl-4-[(tri-t-butylsilyl)methylthio]phenol
2,6-di-t-butyl-4-[(di-t-butylphenylsilyl)methylthio]phenol
2,6-di-methyl-4-[(trimethylsilyl)methylthio]phenol
2,6-di-methyl-4-[(dimethylphenylsilyl)methylthio]phenol
2,6-di-methyl-4-[(dibutylphenylsilyl)methylthio]phenol
2,6-di-methyl-4-[(tri-t-butylsilyl)methylthio]phenol
2,6-di-methyl-4-[(di-t-butylphenylsilyl)methylthio]phenol
2,6-di-ethyl-4-|(trimethylsilyl)methylthio|phenol
2,6-di-ethyl-4-|(dimethylphenylsilyl)methylthio|phenol
2,6-di-ethyl-4-|(tri-t-butylsilyl)methylthio|phenol
2,6-di-ethyl-4-|(di-t-butylphenylsilyl)methylthio|phenol
2,6-di-propyl-4-|(trimethylsilyl)methylthio|phenol
2,6-di-propyl-4-|(dimethylphenylsilyl)methylthio|phenol
2,6-di-isopropyl-4-|(trimethylsilyl)methylthio|phenol
2,6-di-isopropyl-4-|(dimethylphenylsilyl)methylthio|phenol
2,6-di-butyl-4-|(trimethylsilyl)methylthio|phenol
2,6-di-butyl-4-|(dimethylphenylsilyl)methylthio|phenol
2,6-dimethyl-4-|(trimethylsilyl)methyloxy|phenol
2,6-dimethyl-4-|(dimethylphenylsilyl)methyloxy|phenol
2,6-dibutyl-4-|(triethylsilyl)methyloxy|phenol
2,6-dibutyl-4-[(diethylphenylsilyl)methyloxy]phenol
2,6-di-t-butyl-4-|(trimethylsilyl)methyloxy|phenol
2,6-di-t-butyl-4-|(dimethylphenylsilyl)methyloxy|phenol .

A general synthetic scheme for preparing compounds of formula 1 wherein Z is methylene is set forth in Scheme B, wherein all substituents, unless otherwise indicated, are previously defined.

SCHEME B

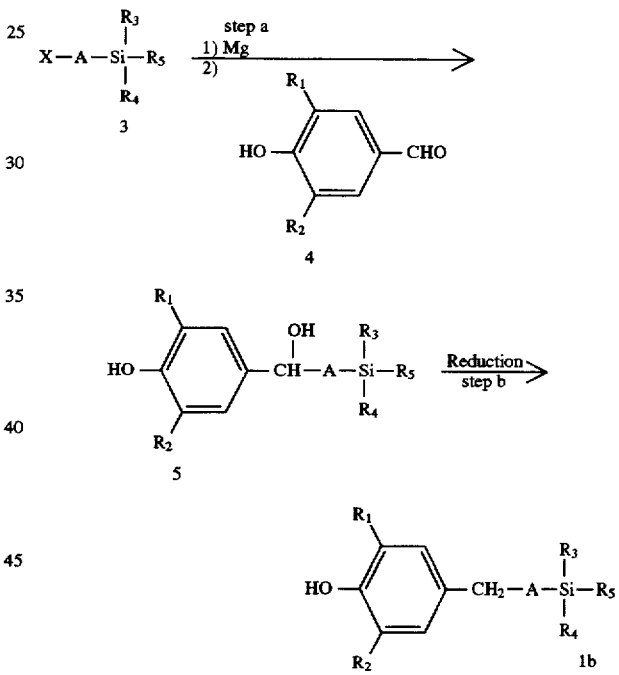

In general, a phenol of structure 1b can be prepared according to Scheme B in a two-step process. In step a, the appropriate haloalkylenesilane of structure 3 is reacted with magnesium metal in a suitable aprotic solvent, such as ethyl ether, in order to form the magnesium halide salt. The magnesium halide salt (Grignard reagent) is then reacted with the appropriate 3,5-dialkyl-4-hydroxybenzaldehyde of structure 4 (or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

Starting materials for use in the general synthetic procedures outlined in Scheme B are readily available or can readily be prepared according to standard techniques and procedures. Where necessary to prevent undesired side reactions, the 1-phenol functionality of the 3,5-dialkyl-4-hydroxy-benzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

EXAMPLE 16

2,6-Dimethyl-4-[2-(trimethylsilyl)ethyl]phenol

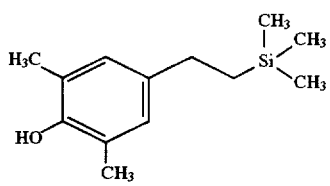

Step a: Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 3,5-dimethyl-4-hydroxybenzaldehyde (1.5 g, 10 mmol) in anhydrous ethyl ether. Stir until reaction is complete. Cool the reaction mixture to 0° C. and add saturated ammonium chloride solution. Separate the ether layer, wash with water and dry (MgSO$_4$). Evaporate to give 4-hydroxy-3,5-dimethyl-α-[(trimethylsilyl)-methyl]benzenemethanol and purify by silica gel chromatrography.

Step b: Mix sodium metal (520 mg, 22.6 mmol) and liquid ammonia (13 mL). To this solution add, by dropwise addition, a solution of 4-hydroxy-3,5-dimethyl-α-[(trimethylsilyl)-methyl]benzenemethanol (2.22 g, 10 mmol) in ethyl alcohol (0.5 g) and ethyl ether (5 ml). After the blue color disappears, cautiously add water (13 mL), extract with ethyl ether, dry (MgSO$_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

SCHEME C

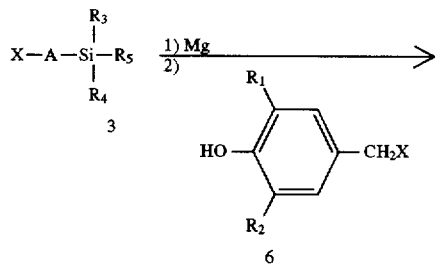

-continued
SCHEME C

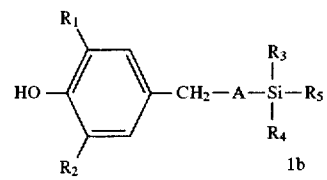

In general, a phenol of structure 1b can be prepared by first reacting the appropriate haloalkylenesilane of structure 3 with magnesium metal in an suitable aprotic solvent, such as ethyl ether, in order to form the magnesium halide salt. The magnesium halide salt (Grignard Reagent) is then reacted with the appropriate 3,5-dialkyl-4-hydroxy-benzylhalide of structure 6 (or a suitably protected derivative) to give the desired phenol of structure 1b.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxybenzylbromide can be converted to the corresponding phenolic starting material by standard hydrolytic procedures.

Where necessary to prevent undesired side reactions, the 1-phenol functionality of the 3,5-dialkyl-4-hydroxybenzylhalide of structure 6 in Scheme C may be blocked prior to the Grignard reaction with a standard phenol blocking agent as described previously in Scheme A.

The following example presents a typical syntheses as described in Scheme C. This example is understood to be illustrative only and is not intended to limit the scope of the present invention in any way.

EXAMPLE 17

2,6-diethyl-4-[2-(trimethylsilyl)ethyl]phenol

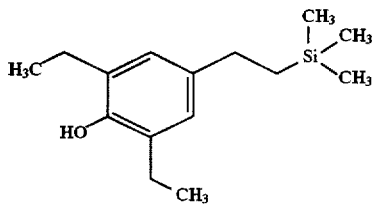

Mix magnesium turnings (240 mg, 10 mmol) and anhydrous ethyl ether under an inert atmosphere. Add a solution of chloromethyltrimethylsilane (1.9 g, 10 mmol) in anhydrous ethyl ether. Stir until the magnesium metal dissolves. Add a solution of 4-bromomethyl-2,6-diethylphenol (2.43 g, 10 mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

The following compounds can be prepared by procedures analogous to those described above in Example 16:
2,6-dipropyl-4-[2-(trimethylsilyl)ethyl]phenol
2,6-dipropyl-4-[2-(dimethylphenylsilyl)ethyl]phenol
2,6-diisopropyl-4-[2-(trimethylsilyl)ethyl]phenol
2,6-diisopropyl-4-[2-(dimethylphenylsilyl)ethyl]phenol
2,6-diisobutyl-4-[2-(trimethylsilyl)ethyl]phenol
2,6-diisobutyl-4-[2-(dimethylphenylsilyl)ethyl]phenol 2,6-dibutyl-4-[2-(trimethylsilyl)ethyl]phenol
2,6-dibutyl-4-[2-(dimethylphenylsilyl)ethyl]phenol
2,6-di-t-butyl-4-[2-(trimethylsilyl)ethyl]phenol
2,6-di-t-butyl-4-[2-(dimethylphenylsilyl)ethyl]phenol
2,6-di-t-butyl-4-[2-(tri-t-butylsilyl)ethyl]phenol
2,6-di-t-butyl-4-[2-(di-t-butylphenylsilyl)ethyl]phenol
2,6-dimethyl-4-[2-(trimethylsilyl)ethyl]phenol
2,6-dimethyl-4-[2-(dimethylphenylsilyl)ethyl]phenol.

It is understood that compounds of formula (1) may exist in various stereoisomeric forms. All stereoisomeric forms which are consistent with the above structural formulas, as interpreted according to standard conventions for expressing stereoisomeric structure, are intended to be included within the scope of the present invention.

Compounds of formula (1), e.g. 2,6-di-alkyl-4-silylphenols, are known in the art. Specifically, compounds of formula (1) are described in U.S. Pat. No. 5,155,250. Preferred compounds of formula (1) are those in which $R_1$ and $R_2$ are $C_4$ alkyl group, $R_3$ and $R_4$ are a $C_1$ alkyl group, A is a $C_1$ alkylene group, and $R_5$ is —$(CH_2)_n$—(Ar) where n is 0 and Ar is phenyl unsubstituted or substituted with one to three substituents selected from the group consisting of hydroxy, methoxy, ethoxy, chloro, fluoro or $C_1$–$C_6$ alkyl. More preferred is the compound 2,6-di-t-butyl-4[(dimethylphenylsilyl)methyl]-thio-phenol.

As used herein, the term "patient" refers to a warm-blooded animal or mammal which is afflicted with a particular VCAM-1 mediated inflammatory disease. It is understood that guinea pigs, dogs, cats, rats, mice, hamsters, rabbits and primates, including humans, are examples of patients within the scope of the meaning of the term.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: asthma, chronic inflammation, rheumatoid arthritis, autoimmune diabetes, transplant rejection and tumor angiogenesis. Compounds of formula (1) which are particularly preferred for treating an inflammatory disease in a patient in need thereof include:

2,6-di-t-butyl-4-[(dimethylphenylsilyl)methylthio]phenol;
2,6-Di-t-butyl-4-[(trimethylsilyl)methylthio]phenol;
2,6-Di-t-butyl-4-[(4-clorophenyldimethylsilyl)methyloxy]phenol;
2,6-Di-t-butyl-4-[(dimethyl-4-fluorophenylsilyl)methyloxy]phenol;
2,6-Di-t-butyl-4-[(dimethyl phenylsilyl)methyloxy]phenol;
2,6-Di-t-butyl-4-[(dimethyl-4-methoxyphenylsilyl)methyloxy]phenol;
2,6-Dimethyl-4-[(dimethylphenylsilyl)-methyloxy]phenol;
2-t-butyl-6-methyl-4-[(dimethylphenylsilyl)methylthio]phenol;
2,6-Di-t-butyl-4-[(dimethyl-2-methoxyphenylsilyl)methyloxy]phenol;
2,6-Di-t-butyl-4-[(dimethyl-2,5-dimethoxyphenylsilyl)methyloxy]phenol;
2,6-Di-t-butyl-4-[(dimethyl-2,3-dimethoxyphenylsilyl)methyloxy]phenol;
2,6-Di-t-butyl-4-[(dimethyl-4-t-butylphenylsilyl)methyloxy]phenol; and
2,6-Di-t-butyl-4-[(benzyldimethylsilyl)methyloxy]phenol.

A "therapeutically effective amount" of a compound of formula (1) is an amount which is effective, upon single or multiple dose administration to the patient, in providing relief of symptoms associated with inflammatory diseases. An "effective vascular cell adhesion molecule-1 inhibiting amount" of a compound of formula (1) is an amount which is effective, upon single or multiple dose administration to the patient, in providing relief of symptoms associated with vascular cell adhesion molecule-1 mediated conditions. As used herein, "relief of symptoms" of an inflammatory disease or vascular cell adhesion molecule-1 mediated conditions refers to decrease in severity over that expected in the absence of treatment and does not necessarily indicate a total elimination or cure of the disease. Relief of symptoms is also intended to include prophylaxis.

In determining the therapeutically effective amount or dose, a number of factors are considered by the attending diagnostician, including, but not limited to: the species of the mammal; its size, age, and general health; the specific disease involved; the degree of or involvment or the severity of the disease; the response of the individual patient; the particular compound administered; the mode of administration; the bioavailability characteristics of the preparation administered; the dose regimen selected; the use of concomitant medication; and other relevant cirmumstances.

A therapeutically effective amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred. Likewise, an effective vascular cell adhesion molecule-1 inhibiting amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

The compounds of this invention are inhibitors of VCAM-1 expression. It is believed that the compounds of this invention exert their inhibitory effect through inhibition of VCAM-1 upregulation by cytokines and thereby prevent or provide relief of symptoms for inflammatory diseases including asthma, chronic inflammation, rheumatoid arthritis, autoimmune diabetes, and the like. However, it is understood that the present invention is not limited by any particular theory or proposed mechanism to explain its effectiveness in an end-use application.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

EXAMPLE 18
Cell Surface ELISA for VCAM-1/ICAM-1

Proliferating human umbilical vein endothelial cells (HUVEC) or human aortic smooth muscle cells (HASMC) from Clonetics (San Diego, Calif.) were plated onto 96-well plates in 100 µL medium per well at 20,000 cells per cm$^2$. The cultures were maintained in growth medium (EGM or SMGM2, Clonetics, San Diego, Calif.) for two days prior to addition of cytokines or drugs. Cytokines plus or minus compounds were added for 20 to 24 hours prior to analysis for adhesion molecule levels. Tumor necrosis factor (Genzyme, Cambridge, Mass.) was added to cultures at 500–1000 units/mL. Interleukin-4 (GIBCO-BRL, Gaithersburg, Md.) was added to cultures at 100–200 pg/mL. (Additions were made by transferring 100 µL of cytokines plus compounds serially diluted on a separate 96-well plate into the plates containing cells. The medium on the cultures was not exchanged prior to addition of effectors). The culture medium was removed, and the monolayers were washed twice with Hanks buffered saline solution (HBSS) at room temperature. The primary antibody (anti-human VCAM-1 from Upstate Biotechnology, Inc., Lake Placid, N.Y. or anti-human ICAM-1 from Immunotech, Inc., Westbrook, Me.) was added to each well (1 µg/mL in HBSS plus 5% newborn calf serum, GIBCO-BRL, Gaithersburg, Md.) and incubated at 37° C. for 1 hr. The wells were washed twice with HBSS, then 100 µL of a 1/1000 dilution of goat anti-mouse IgG conjugated to horse radish peroxidase (BioRad, Hercules, Calif.) in HBSS plus 5% newborn calf serum was added to each well and incubated for 1 hr at 37° C. The wells were washed three times with HBSS, then 100 µL of TMB substrate (BioRad, Hercules, Calif.) was added to each well. The reaction was stopped after blue color developed by addition of 50 µL of 1N H$_2$SO$_4$. Absorbance is measured at 450 nm with a plate reader. IC$_{50}$ values were determined from curves of absorbance values obtained from serial dilutions of compounds (dissolved in dimethyl sulfoxide).

The IC$_{50}$ value is defined as the drug concentration that inhibits the cytokine-induced adhesion molecule expression by 50%. Maximal values for adhesion molecule expression in cytokine-induced cultures was subtracted from the basal level of adhesion molecule expression (minus cytokines) in the cultures to determine the level of induction. VCAM-1 was typically induced about 5–7 fold. ICAM-1 was typically induced 5–10 fold. Each drug concentration was tested in quadruplicate wells. Single point tests of compounds at 50 µM were assayed as described for IC$_{50}$ determinations, except that the data represent the level of inhibition without correction for basal expression. (Basal adhesion molecule expression was 10–20% of the total induced expression).

Table 1 summarizes the ability of various compounds of this invention to inhibit VCAM-1 using human aortic smooth muscle cells (HASMC). In these experiments, the cells were coincubated with interleukin-4 and the compounds listed about 20 hr before assaying cell surface VCAM-1 levels. Each column represents a separate experiment.

TABLE 1

| Cmpd. No. (MDL No.) | HSMC-1 (% inh. 50 µM) | HSMC-2 (% inh. 50 µM) | HSMC-3 (% inh. 50 µM) | VCAM-1 (Avg.) |
| --- | --- | --- | --- | --- |
| 28,235 | 7.8 | 18.0 | 42.0 | 22.6 |
| 29,353 | 58.0 | 60.0 | 46.0 | 54.7 |
| 103,719 |  | 49.0 | 42.0 | 45.5 |
| 103,902 | 49.0 | 60.0 | 43.0 | 50.7 |
| 104,280 | 54.7 | 63.0 | 44.0 | 53.9 |
| 104,518 | 4.4 | 47.0 | 26.0 | 25.8 |
| 105,074 | 28.3 | 52.0 | 47.0 | 42.4 |

Table 2 summarizes the ability of various compounds of this invention to selectively inhibit VCAM-1 or to inhibit both VCAM-1 and ICAM-1 using proliferating human umbilical vein endothelial cells (HUVEC). In these experiments, the cells were coincubated with tumor necrosis factor-alpha along with the indicated compounds about 20 to 24 hr before assaying cell surface adhesion molecule expression.

TABLE 2

| Cmpd. No. (MDL No.) | VCAM-1 (% inh. 50 µM)* | ICAM-1 (% inh. 50 µM)@ |
|---|---|---|
| 28,235 | 4.3 | (3.0) |
| 29,353 | 8.7 | 6.0 |
| 103,719 | 17.0 | 77.0 |
| 103,902 | 25.3 | 39.0 |
| 104,280 | 27.3 | 22.0 |
| 104,518 | (1.0) | 78.0 |
| 105,074 | 20.0 | (8.0) |

*Average of three runs
@Average of two runs

Table 3 illustrates the activity of selected compounds when eight serial dilutions of drug were tested against cytokine induction of VCAM-1 expression in both vascular endothelial and smooth muscle cells. Subtraction of basal VCAM-1 expression was also used in the calculation of $IC_{50}$ values. Each compound was also tested in a similar manner for ICAM-1 inhibition. No inhibition of ICAM-1 was detected (up to 100 µM) in vascular smooth muscle cells. In vascular endothelial cells, only MDL 103,902 showed significant inhibition of ICAM-1 expression at 50 and 100 µM, which could be accounted for by the loss of cell adherence to the tissue culture surface as observed with a microscope.

TABLE 3

| Compound No. (MDL No.) | VCAM-1, HUVEC ($IC_{50}$, µm) | VCAM-1, HSMC ($IC_{50}$, µm) |
|---|---|---|
| 29,353 | 19 | 10 |
| 103,902 | 11 | 5 |
| 105,074 | 12 | 40 |

EXAMPLE 19
In Vivo Inhibition of VCAM-1 Upregulation by MDL 29,353 in Rabbit Aorta New Zealand white rabbits were fed a diet of chow plus or minus 0.4% MDL 29,353 for three weeks prior to challenge with lipopolysaccharide (LPS, 40 µg/animal, i.v. ear vein). The aorta was removed from each animal 4 hr after LPS injection and rinsed briefly in phosphate buffered saline. VCAM-1 was immunohistochemistry was performed by incubating the tissues with RB1/9 antibody (mouse anti-rabbit VCAM-1) at 4° C. overnight. The bound RB1/9 was detected using a biotinylated goat anti-mouse secondary antibody (60 min, RT). VCAM-1 staining was accomplished by addition of streptavidin-alkaline phosphatase conjugate (30 min, RT) followed by an incubation with BT Red (Biotec, 10, RT). Images of the stained tissues were captured using an image analysis system for determination of the percentages of the aortic endothelium showing immunoreactivity with anti-VCAM antibody.

In vivo activity of these compounds can also be assessed in other models of inflammation predicted to involve elevated VCAM-1 levels. One such model for respiratory diseases, such as asthma, is an ovalbumin-sensitized model. Kung, T. T. et al., *Int. Arch. Allergy Immunol.* 105, 83–90 (1994). This model of pulmonary inflammation is IgE mediated and involves eosinophillia (as does the asthmatic human). The bronchial alveolar lavage (BAL) fluid obtained from experimental animals can be assessed for a number of parameters, including soluble adhesion molecule expression and leukocyte accumulation. Adhesion molecule expression can be assessed by immunohistochemistry within the tissues, especially the lung, of experimental animals. The effect of the claimed compounds, such as MDL 29,353, should be to suppress the upregulation of VCAM-1 expression and inhibit eosinophil accumulation in the BAL fluid. The inhibitors could be tested in a rat model of adjuvant arthritis, which has been previously shown to respond to anti-ICAM-1 monoclonal antibodies. Iigo, Y. et al., *J. Immunol.* 147, 4167–4171 (1991). In this model, adhesion molecule expression would be assessed in the limbs (joints) of experimental animals. For autoimmune diabetes, one could test the compounds for their ability to delay the onset or prevent adoptive transfer of disease in the NOD mouse model. Heinke, E. W. et al., *Diabetes* 42, 1721–1730 (1993); Baron, J. L. et al., *J. Clin. Invest.* 93, 1700–1708 (1994). Furthermore, one can monitor the level of VCAM-1 expression in the tissues (e.g. pancreas) as well as monitor the development of diabetes in the experimental animal. Therapeutic potential for transplant rejection can be assessed by monitoring cardiac allograft survival (Balb/c hearts transplanted into C3H/He recipients. Isobe, M. et al., *J. Immunol.* 153, 5810–5818 (1994). In vivo administration of anti-VCAM-1 and anti-VLA-4 monoclonal antibodies induces immunosuppression to cardiac allografts and soluble antigens in this mouse model. Compound effects on tumor metastasis and angiogenesis can be evaluated in a number of models. These can include the B16 (murine) and M24 met (human) melanoma models for experimental metastasis. Fidler, L. J., *Cancer Res.* 35, 218–224 (1975); Meuller, B. M. et al., *Cancer Res.* 51, 2193–2198. Activity of the compounds can be assessed by their effect on the number of lung metastases which develop, as well as their effect on VCAM-1 expression in the lung as described above for the mouse respiratory model. A model for evaluating anti-angiogenic compounds which can be used to test the compounds involves monitoring the vascular response to a mixture of angiogenic factors mixed with basement membrane proteins injected subcutaneously in mice. Passaniti, A. et al., *Lab. Invest.* 67, 519–528 (1992). Angiogenesis is scored by the number of vessels recruited into the matrigel and by the hemoglobin content of the gels. Adhesion molecule expression and accumulation of leukocyte can be determined by immunohistochemical methods as in all of the above examples.

Results

The claimed compounds inhibit cytokine-induced upregulation of VCAM-1 gene expression in vascular cells in vitro. Selective inhibition of VCAM-1 expression as compared with another cytokine-inducible adhesion molecule, ICAM-1, has been demonstrated for certain members of the claimed compounds (Table 3). In vivo experiments show that MDL 29,353, when adequately accumulated, can inhibit the LPS induced level of VCAM-1 expression in rabbit aortic endothelium (FIG. 1). This experiment also demonstrates that the compounds have oral activity.

What is claimed is:

1. A method of inhibiting cytokine-induced expression of vascular cell adhesion molecule-1 in a patient in need thereof which comprises administering to said patient an effective vascular cell adhesion molecule-1 inhibiting amount of a compound of the formula

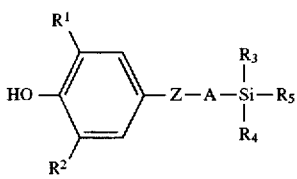

wherein

R$_1$, R$_2$, R$_3$ and R$_4$ are each independently a C$_1$–C$_6$ alkyl group;

Z is a thio, oxy or methylene group;

A is a C$_1$–C$_4$ alkylene group;

R$_5$ is a C$_1$–C$_6$ alkyl or —(CH$_2$)$_n$—(Ar)

wherein n is an integer 0, 1, 2 or 3; and Ar is phenyl or naphthyl unsubstituted or substituted with one to three substituents selected from the group consisting of hydroxy, methoxy, ethoxy, chloro, fluoro or C$_1$–C$_6$ alkyl.

2. A method according to claim 1 wherein R$_1$ and R$_2$ are tertiarybutyl.

3. A method according to claim 2 wherein R$_3$ and R$_4$ are methyl.

4. A method according to claim 3 wherein A is methylene.

5. A method according to claim 4 wherein Z is thio.

6. A method according to claim 4 wherein Z is oxy.

7. A method according to claim 1 wherein the compound is 2,6-di-t-butyl-4-[(dimethylphenylsilyl)methylthio]phenol.

8. A method according to claim 1 wherein the compound is 2,6-Di-t-butyl-4-[(trimethylsilyl)methylthio]phenol.

9. A method according to claim 1 wherein the compound is 2,6-Di-t-butyl-4-[(4-clorophenyldimethylsilyl)methyloxy]phenol.

10. A method according to claim 1 wherein the compound is 2,6-Di-t-butyl-4-[(dimethyl-4-fluorophenylsilyl)methyloxy]phenol.

11. A method according to claim 1 wherein the compound is 2,6-Di-t-butyl-4-[(dimethylphenylsilyl)methyloxy]phenol.

12. A method according to claim 1 wherein the compound is 2,6-Di-t-butyl-4-[(dimethyl-4-methoxyphenylsilyl)methyloxy]phenol.

13. A method according to claim 1 wherein the compound is 2,6-Dimethyl-4-[(dimethylphenylsilyl)methyloxy]phenol.

14. A method according to claim 1 wherein the compound is 2-t-butyl-6-methyl-4-[(dimethylphenylsilyl)methylthio]phenol.

15. A method according to claim 1 wherein the compound is 2,6-Di-t-butyl-4-[(dimethyl-2-methoxyphenylsilyl)methyloxy]phenol.

16. A method according to claim 1 wherein the compound is 2,6-Di-t-butyl-4-[(dimethyl-2,5-dimethoxyphenylsilyl)methyloxy]phenol.

17. A method according to claim 1 wherein the compound is 2,6-Di-t-butyl-4-[(dimethyl-2,3-dimethoxyphenylsilyl)methyloxy]phenol.

18. A method according to claim 1 wherein the compound is 2,6-Di-t-butyl-4-[(dimethyl-4-t-butylphenylsilyl)methyloxy]phenol.

19. A method according to claim 1 wherein the compound is 2,6-Di-t-butyl-4-[(benzyldimethylsilyl)methyloxy]phenol.

20. A method according to claim 1 wherein the compound is 2,6-Di-t-butyl-4-[(dimethyl-p-methoxybenzylsilyl)methyloxy]phenol.

21. A method of treating a patient afflicted with a chronic inflammatory disease, said method comprising administering to said patient a therapeutically effective amount of a compound of the formula

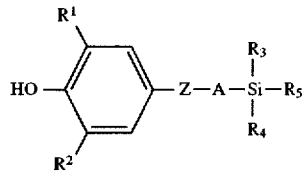

wherein

R$_1$, R$_2$, R$_3$ and R$_4$ are each independently a C$_1$–C$_6$ alkyl group;

Z is a thio, oxy or methylene group;

A is a C$_1$–C$_4$ alkylene group;

R$_5$ is a C$_1$–C$_6$ alkyl or —(CH$_2$)$_n$—(Ar)

wherein n is an integer 0, 1, 2 or 3; and Ar is phenyl or naphthyl unsubstituted or substituted with one to three substituents selected from the group consisting of hydroxy, methoxy, ethoxy, chloro, fluoro or C$_1$–C$_6$ alkyl.

22. A method according to claim 21 wherein R$_1$ and R$_2$ are tertiarybutyl.

23. A method according to claim 22 wherein R$_3$ and R$_4$ are methyl.

24. A method according to claim 23 wherein A is methylene.

25. A method according to claim 24 wherein Z is thio.

26. A method according to claim 24 wherein Z is oxy.

27. A method according to claim 21 wherein the compound is 2,6-di-t-butyl-4-[(dimethylphenylsilyl)methylthio]phenol.

28. A method according to claim 21 wherein the compound is 2,6-Di-t-butyl-4-[(trimethylsilyl)methylthio]phenol.

29. A method according to claim 21 wherein the compound is 2,6-Di-t-butyl-4-[(4-clorophenyldimethylsilyl)methyloxy]phenol.

30. A method according to claim 21 wherein the compound is 2,6-Di-t-butyl-4-[(dimethyl-4-fluorophenylsilyl)methyloxy]phenol.

31. A method according to claim 21 wherein the compound is 2,6-Di-t-butyl-4-[(dimethylphenylsilyl)methyloxy]phenol.

32. A method according to claim 21 wherein the compound is 2,6-Di-t-butyl-4-[(dimethyl-4-methoxyphenylsilyl)methyloxy]phenol.

33. A method according to claim 21 wherein the compound is 2,6-Dimethyl-4-[(dimethylphenylsilyl)methyloxy]phenol.

34. A method according to claim 21 wherein the compound is 2-t-butyl-6-methyl-4-[(dimethylphenylsilyl)methylthio]phenol.

35. A method according to claim 21 wherein the compound is 2,6-Di-t-butyl-4-[(dimethyl-2-methoxyphenylsilyl)methyloxy]phenol.

36. A method according to claim 21 wherein the compound is 2,6-Di-t-butyl-4-[(dimethyl-2,5-dimethoxyphenylsilyl)methyloxy]phenol.

37. A method according to claim 21 wherein the compound is 2,6-Di-t-butyl-4-[(dimethyl-2,3-dimethoxyphenylsilyl)methyloxy]phenol.

38. A method according to claim 21 wherein the compound is 2,6-Di-t-butyl-4-[(dimethyl-4-t-butylphenylsilyl)methyloxy]phenol.

39. A method according to claim 21 wherein the compound is 2.6-Di-t-butyl-4-[(benzyldimethylsilyl)methyloxy]phenol.

40. A method according to claim 21 wherein the compound is 2.6-Di-t-butyl-4-[(dimethyl-p-methoxybenzylsilyl)methyloxy]phenol.

41. A method according to claim 21 wherein the inflammatory disease is asthma.

42. A method according to claim 21 wherein the inflammatory disease is chronic inflammation.

43. A method according to claim 21 wherein the inflammatory disease is rheumatoid arthritis.

44. A method according to claim 21 wherein the inflammatory disease is autoimmune diabetes.

45. A method according to claim 21 wherein the inflammatory disease is transplant rejection.

46. A method according to claim 21 wherein the inflammatory disease is tumor angiogenesis.

* * * * *